(12) United States Patent  (10) Patent No.: US 7,389,744 B2
Zhang et al.  (45) Date of Patent: Jun. 24, 2008

(54) METHOD AND APPARATUS FOR TRACKING A LABORATORY ANIMAL LOCATION AND MOVEMENT

(76) Inventors: Jingxi Zhang, 1403 Melbourne St., Foster City, CA (US) 94404; Yang Zhang, 1403 Melbourne St., Foster City, CA (US) 94404; Huifang Ni, 1403 Melbourne St., Foster City, CA (US) 94404

( * ) Notice: Subject to any disclaimer, the term of this patent is extended or adjusted under 35 U.S.C. 154(b) by 100 days.

(21) Appl. No.: 11/308,488

(22) Filed: Mar. 29, 2006

(65) Prior Publication Data

US 2007/0236356 A1 Oct. 11, 2007

(51) Int. Cl.
*A01K 1/03* (2006.01)
(52) U.S. Cl. ..................................... 119/421
(58) Field of Classification Search ......... 119/416–419, 119/421, 712, 174, 908; 340/573.1, 573.3; 250/221; 600/595
See application file for complete search history.

(56) References Cited

U.S. PATENT DOCUMENTS

| | | | |
|---|---|---|---|
| 3,304,911 A | 2/1967 | Hataka et al. | |
| 3,439,358 A | 4/1969 | Salmons | |
| 3,540,413 A | 11/1970 | Castaigne | |
| 3,633,001 A | 1/1972 | Vajnovszky | |
| 3,656,456 A | 4/1972 | Stigmark et al. | |
| 3,974,798 A | 8/1976 | Meetze, Jr. | |
| 4,337,726 A | 7/1982 | Czekajewski et al. | |
| 4,574,734 A | 3/1986 | Mandalaywala et al. | |
| 4,968,974 A | 11/1990 | Sakano | |
| 5,608,209 A | 3/1997 | Matsuda | |
| 5,717,202 A | 2/1998 | Matsuda | |
| 5,915,332 A | 6/1999 | Young | |
| 6,062,224 A * | 5/2000 | Kissinger et al. | 128/897 |
| 2005/0066910 A1* | 3/2005 | Tecott et al. | 119/421 |
| 2007/0107666 A1* | 5/2007 | Salzmann et al. | 119/421 |
| 2007/0125313 A1* | 6/2007 | Fleetwood | 119/721 |

\* cited by examiner

*Primary Examiner*—T. Nguyen

(57) ABSTRACT

A system for tracking the laboratory animal position and movement in a walled enclosure or cage for observation and evaluation is disclosed. The system consists of a plate placed on the bottom of the cage whereon multiple electrodes are configured as column-row two-dimensional electrode array, an electronic circuit detecting and measuring the capacitance between said electrodes, and a microprocessor determining the animal's location. The electronic circuit repeatedly measures the capacitance between the electrodes in a sequential manner. The animal's location and movement is determined by detecting the changes in capacitance on said plate.

11 Claims, 7 Drawing Sheets

METHOD AND APPARATUS FOR TRACKING A LABORATORY ANIMAL LOCATION AND MOVEMENT

BACKGROUND OF THE INVENTION

Locomotion function is one of the important behavior parameters in animal research for human neurodegenerative diseases such as Parkinson's disease, Huntington's disease, and Alzheimer's disease. Neurodegenerative animal models have been well-established in rodents. Animal models with such diseases exhibit characteristic motoric deficits including declined movement activity, decreased movement speed, and reduced traveling distance. With an effective drug treatment, the animal locomotion function could be recovered to a great extent. Therefore, automated logging of the animal's locomotion function is essential in the pharmaceutical laboratory.

A number of inventors proposed methods to detect laboratory animal dynamic motion activity. The Stigmark et al U.S. Pat. No. 3,656,456 provides a system to monitor motion activity by detecting electrode capacity imbalance across a transformer bridge which results from animal movement in the environment. The Castaigne U.S. Pat. No. 3,540,413, the Vajnoszky U.S. Pat. No. 3,633,001 and the Meetze U.S. Pat. No. 3,974,798 disclose methods to detect laboratory animal motion activities by measuring the conductance of animals in contact with electrodes.

Methods of detecting laboratory animal locations are also provided by many other inventors. The earlier method disclosed by U.S. Pat. No. 3,304,911 (Hakata, et al) uses a pair of movable infrared light receivers to track animal locations in a square field. Salmons U.S. Pat. No. 3,439,358 utilizes multiple receiving antennae to detect animal location using the antennae's proximity to the animal. Other inventors report methods to detect animal location in a rectangular cage by employing infrared transmitter and receiver arrays; these inventors include Czekajewski, et al (U.S. Pat. No. 4,337,726), Mandalaywala, et al (U.S. Pat. No. 4,574,734), Matsuda (U.S. Pat. Nos. 5,608,209 and 5,717,202) and Young (U.S. Pat. No. 5,915,332). Sakano U.S. Pat. No. 4,968,974 also proposes an infrared position detection system for an animal in a cylindrical cage.

An advantage of the present invention is the provision of an inexpensive apparatus that can easily adapt to the conventional laboratory animal cage, the so-called animal home cage, without any special enclosures or modifications to the existing cage.

BRIEF SUMMARY OF THE INVENTION

It is an objective of the present invention to provide an apparatus which is inexpensive, can easily adapt to a conventional animal cage, and has a measurement method for determining the laboratory animal's location and movement in the cage. The apparatus is comprised of a plate placed on the bottom of the cage whereon multiple electrode pairs are configured as a two-dimensional electrode array, an electronic circuit detecting and measuring the capacitance between said electrodes, and a microprocessor determining the animal location. The electrodes are connected as rows and columns groups. An electric signal generator in the capacitance detection circuit sends an excitation signal to the electrode array. The capacitance detection circuit receives the signal from each electrode row or column group in a sequential manner. The signals received are amplified, rectified, filtered and sampled by a microprocessor. When the animal is present in the cage and above the electrode plate, the signal on the electrodes induced by the excitation signal is altered due to capacitance change caused by proximity of the animal body.

The microprocessor compares the signal with the pre-stored reference signal to detect the capacitor change. By determining the capacitance changes among the electrodes, the animal's x-y coordinate can be determined.

DETAILED DESCRIPTION OF THE INVENTION

Figure 1:
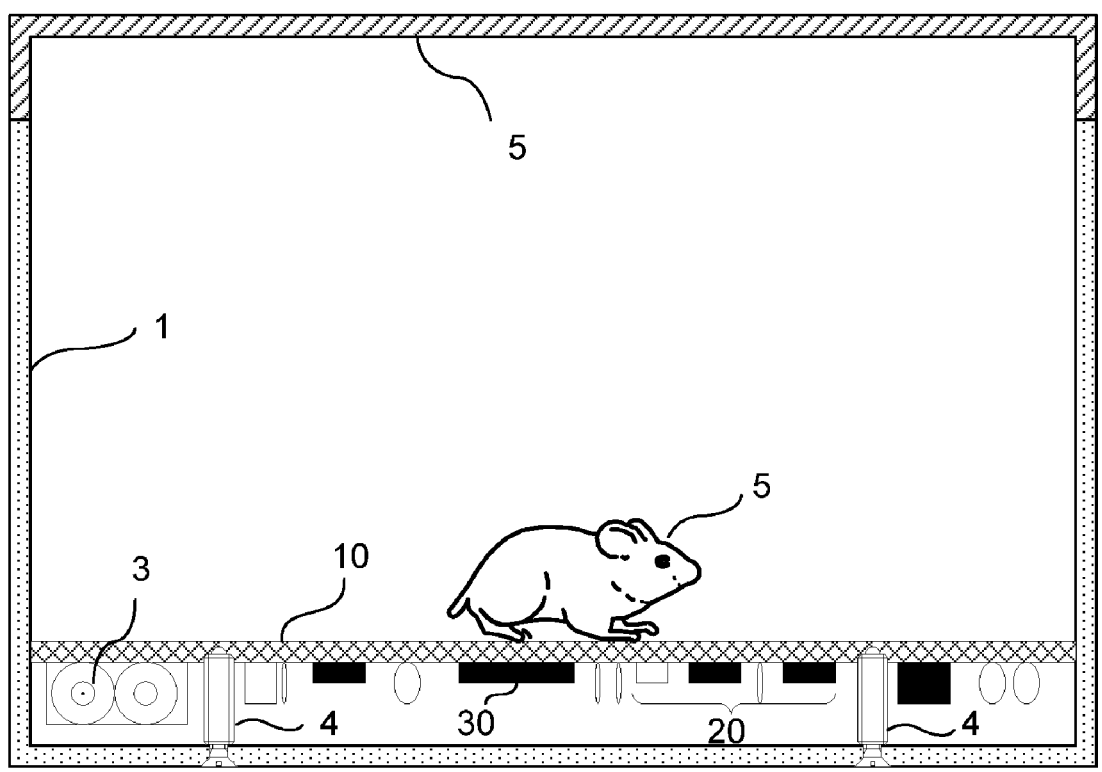
FIG. 1 is a drawing of an animal enclosure according to teachings of the present invention.

Referring to the Figures, the preferred embodiment of the present invention is described in detail. FIG. 1, a cage or enclosure 1, usually made with transparent polymetacrylate-glass (Plexiglas) material, provides the laboratory animal 5 for observation and evaluation a bounded activity space. An electrode plate 10 is placed on the bottom of the cage supported by the fastening stands 3. The electrode plate 10 and its electrode arrangement will be described in detail later. On the bottom side of the electrode plate are the electronic components 20 and microprocessor 30 for detecting animal location and movement. The cage is open at top and is secured by a top cover 2 made of Plexiglas or metal with ventilation openings and food/water delivery attachments, details of which are beyond the scope of this invention.

Figure 2:
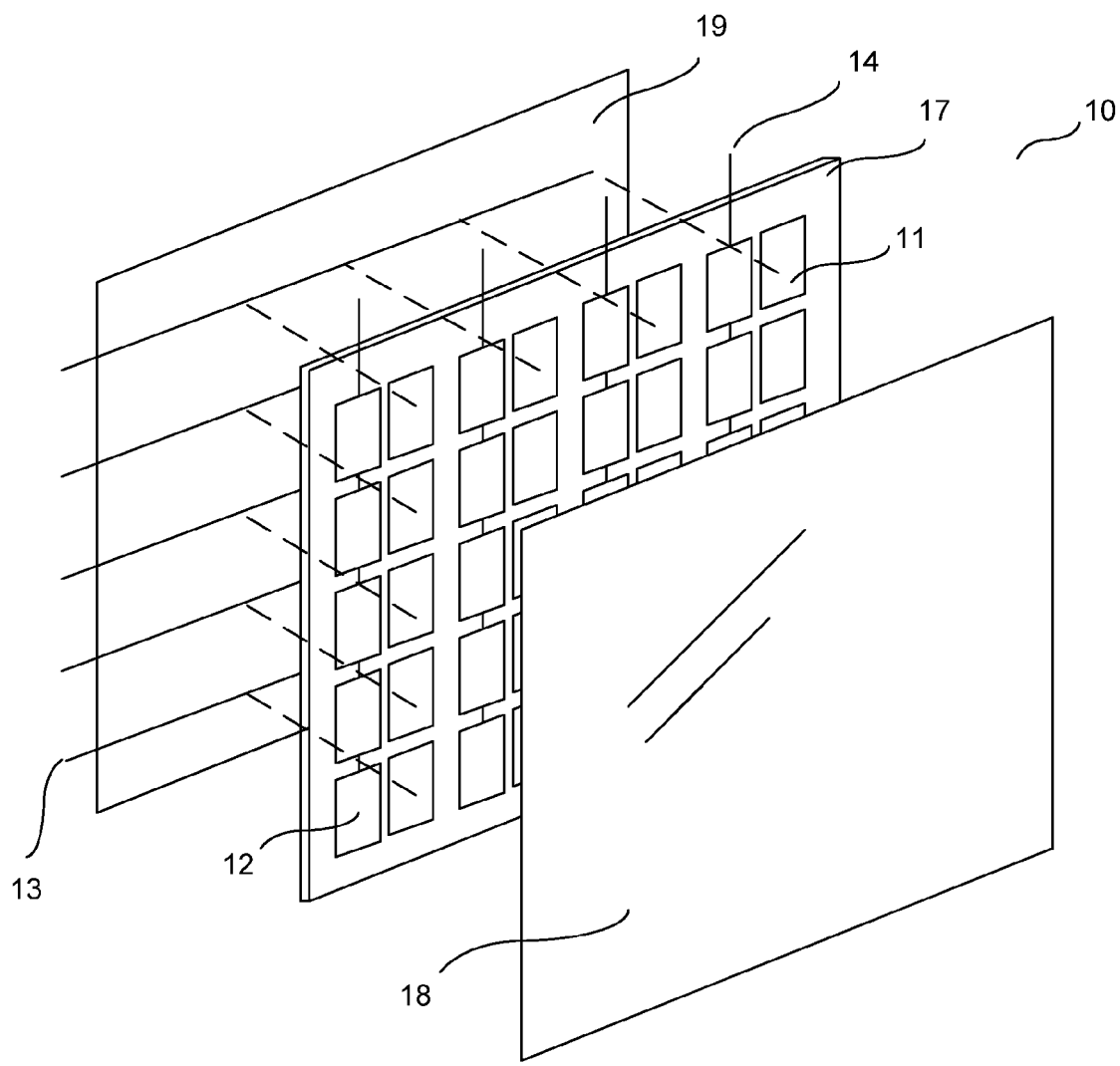
FIG. 2 illustrates the electrode plate structure.
Figure 3:
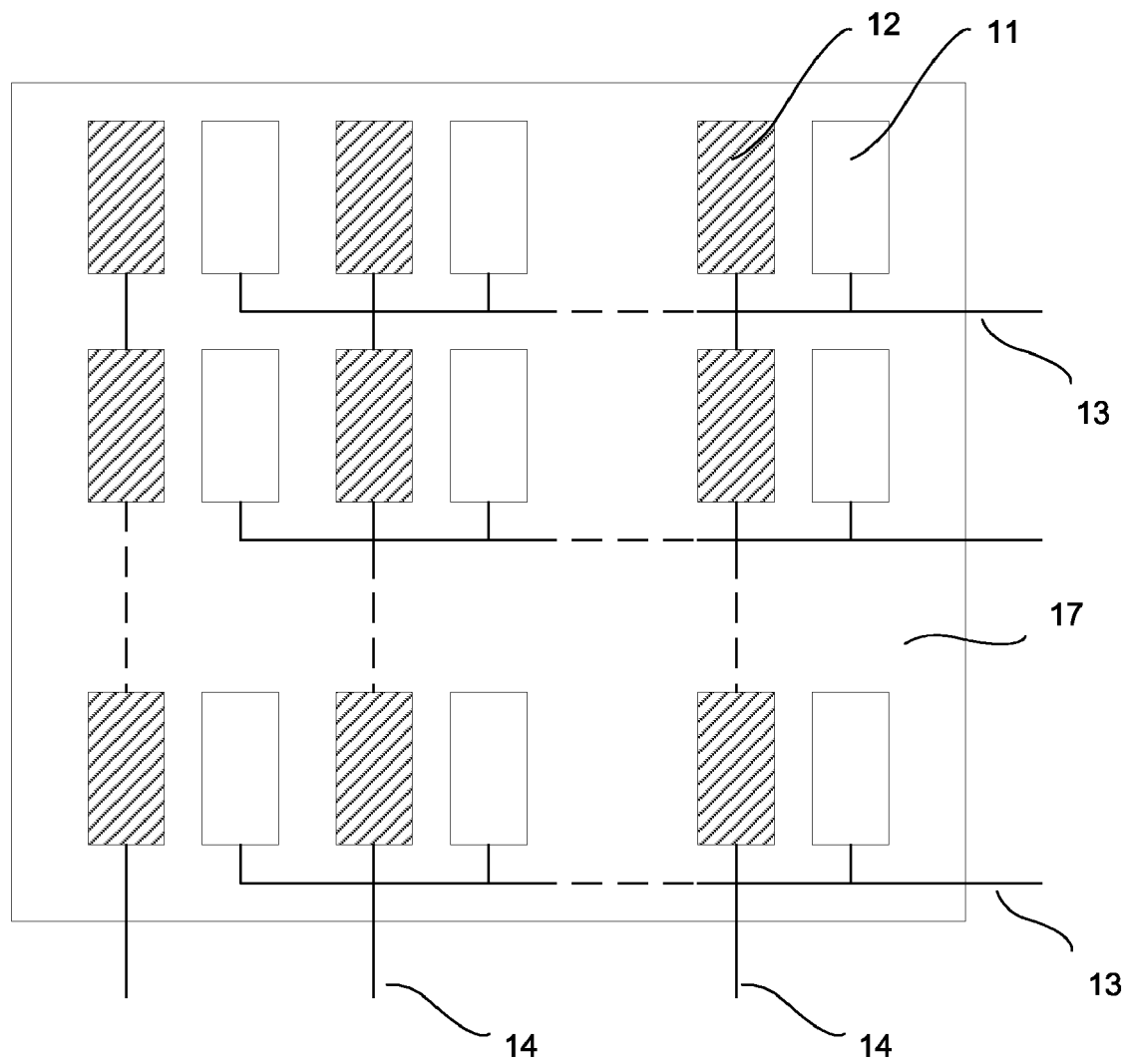
FIG. 3 demonstrates the row and column electrode connections.
Figure 4:
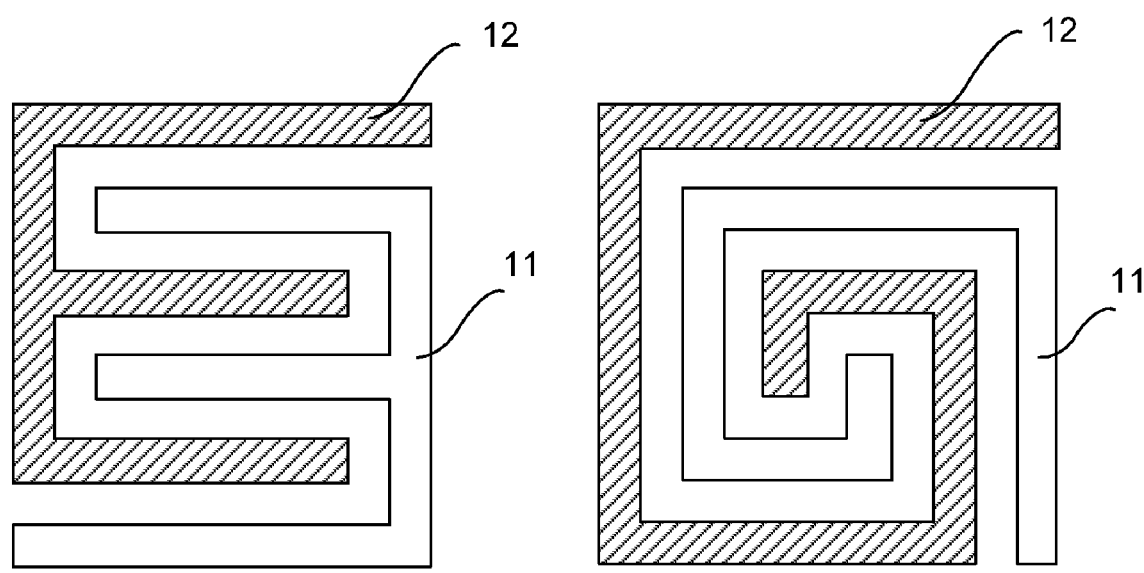
FIG. 4 shows some samples of electrode configuration patterns.

FIG. 2 illustrates the structure of the electrode plate 10. The rectangular-shaped supporting plate 17, whose dimensions match those of the animal cage floor, is made of electrical insulating material. The flat electrodes 11 and 12 are laid out on the surface of the supporting plate. The electrodes are insulated from each other and separated by a small predetermined space. Note that the figure is a simplified drawing to illustrate the electrode arrangement, and the dimensions may not be drawn to scale. The electrodes are connected as rows (11) by the wires 13 and columns (12) by the wires 14 as shown in FIG. 3. The electrodes connected in rows are paired with neighboring electrodes connected in columns to form the electrode matrix. Neighboring row-connected and column-connected electrodes may be further intertwined into inter-digitated patterns to increase the sensitivity of animal detection; example embodiments are shown in FIG. 4a, the comb-like pattern, and FIG. 4b, the spiral pattern. The intertwined electrodes can be made using the printed circuit board (PCB) technique. The wires 13 connecting the rows of electrodes 11 are further routed to a row multiplexer 21 while the wires 14 connecting the columns of electrodes 12 are further routed to a column multiplexer 22. As shown in FIG. 2, a thin insulation layer 18 is on top of the electrode plate to prevent the animal's paws from directly contacting the electrodes and also to physically protect the electrode array from damage by animal paws. An electrical conducting sheet 19 is on the backside of the electrode plate for shielding the electrode plate 10 from interference of other objects which may be close to the bottom of said electrode plate. The electrode plate is connected to the shield signal from the shield signal driver 25.

Figure 5:
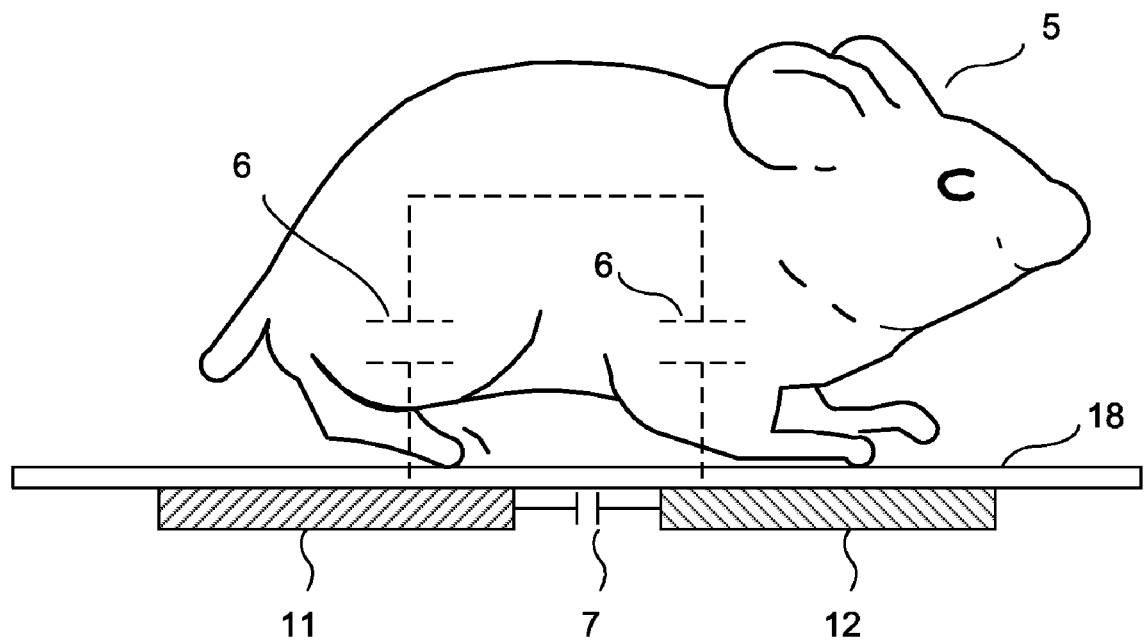
FIG. 5 visualizes the relationship between the electrodes and the capacities resulting from the animal body.

In case the animal is absent from the cage, there is capacity 7 existing in between each electrode and surrounding electrodes as shown on FIG. 5. When the animal is present in the cage and above the electrode plate, there are capacities 6 in between the electrodes and the animal body. The capacities 6 are in parallel with the original capacity 7 in between the electrodes and as a result, the total capacitance of the electrode under the animal body increases, relative to the capacitances of the surrounding electrodes. By detecting the capacity changes of the electrodes connected in rows, the animal location on the row ordinate can be deduced. Using the same method, by detecting the capacity changes of the electrodes connected in columns, the animal location on the column ordinate can be deduced and thus animal's x and y coordinate on the electrode plate is determined.

Figure 6:
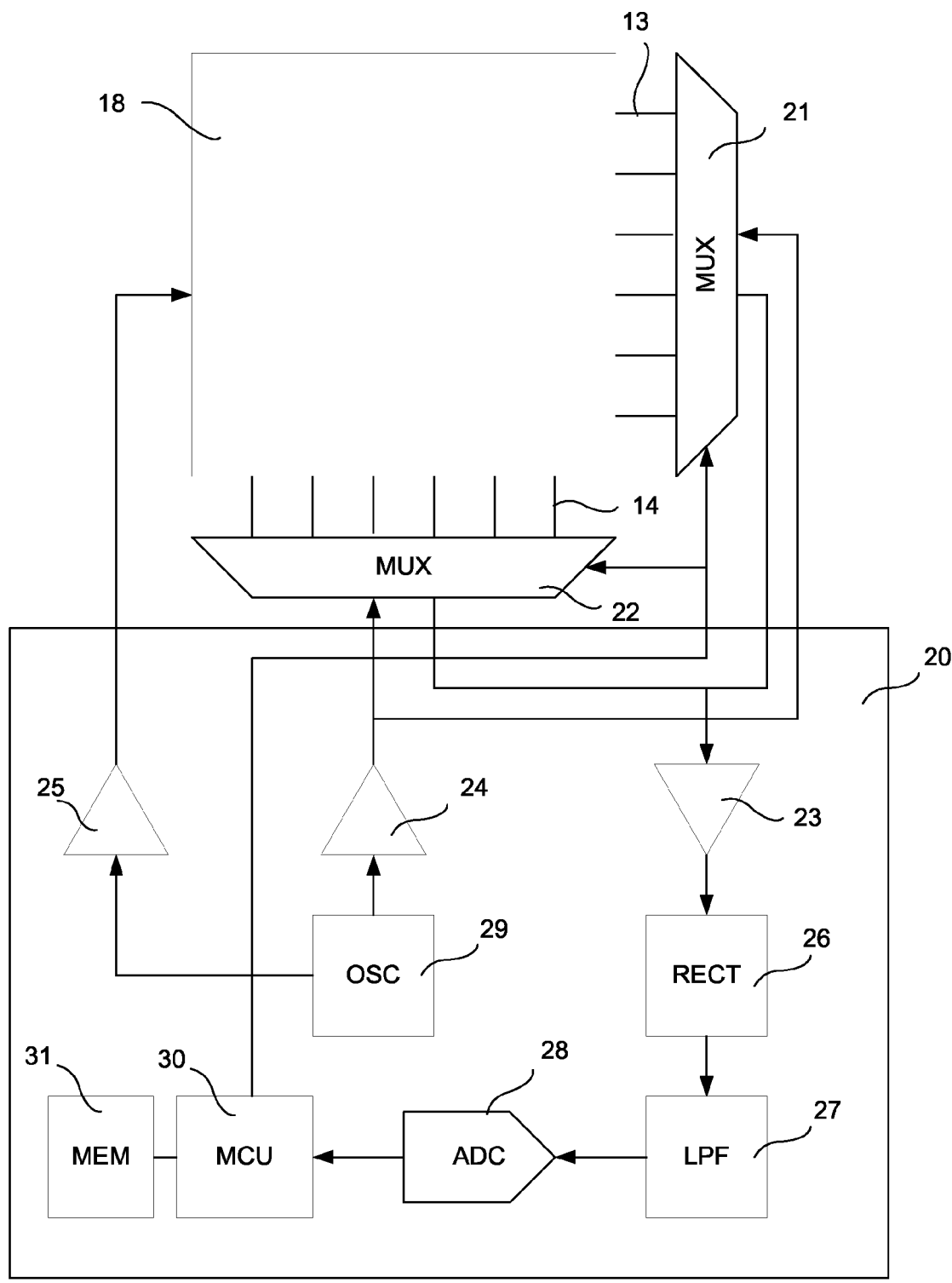
FIG. 6 is an electronic schematic diagram illustrating the circuitry of an embodiment according to the teachings of the present invention.

The capacity detection means is shown on FIG. 6. The electrodes connected in rows through the wires 13 are connected to the multiplexer 21 and the electrodes connected in columns through the wires 14 are connected to the multiplexer 22. The multiplexer 21 and multiplexer 22 are controlled by the microprocessor 30 in such a way that only one row or one column of the electrodes is routed to the capacity detection circuit 20 at any moment. When the apparatus starts, the first row of electrodes is routed to said capacity detection circuit. Then each row of electrodes followed by each column of electrodes is routed to the capacity detection circuit one by one, separated by a predetermined short time interval. After the last column of electrodes is executed, the procedure repeats again from the first row of electrodes. The time interval in between each route is determined by the capacitance data sampling rate.

Figure 7:
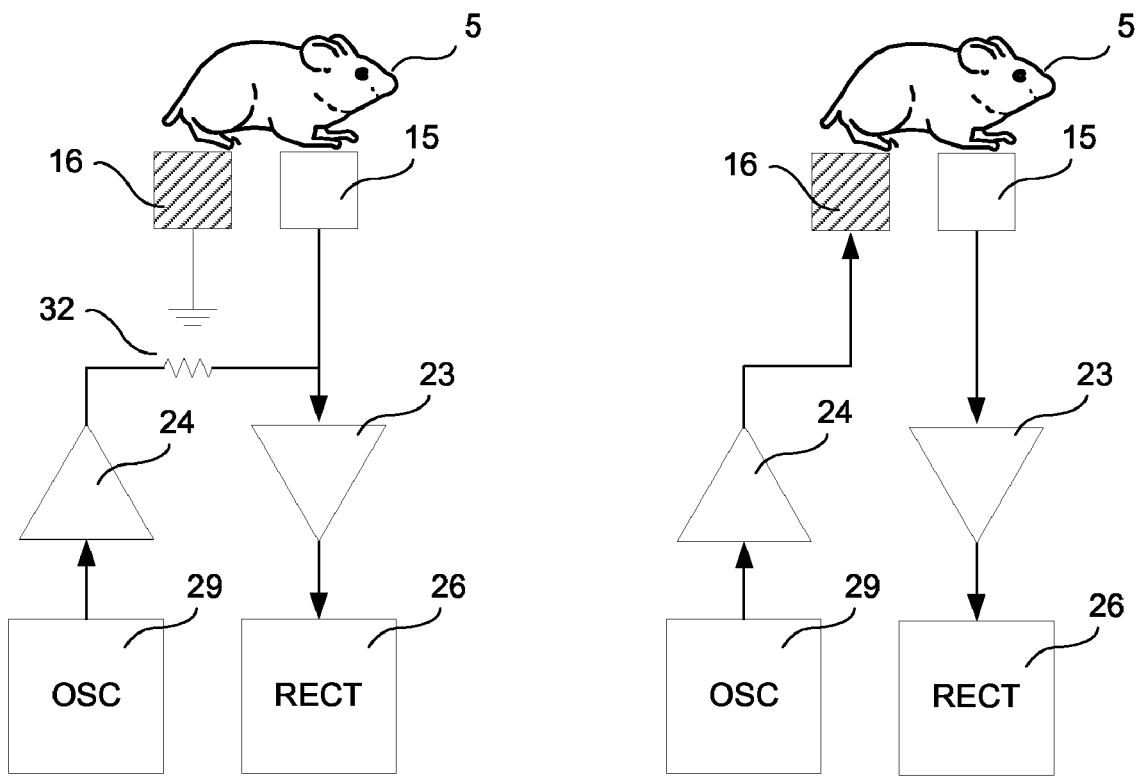
FIG. 7 shows the two configurations of the capacitance detection input and the excitation signal output.

The excitation source of the capacity measurement is the oscillator 29 which generates high purity sine waves at 120 KHz at the preferred embodiment. The excitation wave signal is delivered to the electrode plate through multiplexer 21 and 22 after it is amplified by the amplifier 24. The signal received from the electrodes is also routed to the amplifier 23 by multiplexer 21 and 22. The relationship between the excitation signal and the received signal is shown in FIG. 7a and FIG. 7b, and will be described later. The amplified received signal is rectified by a rectifier 26. The rectified signal is then sent to a low pass filter 27 before it is sent to the analog-to-digital converter (ADC) 28. The low pass filter 27 removes the high frequency interference and limits the signal to a low frequency band representing the animal movement by a predetermined cut-off frequency. The ADC 28 converts the received signal into digital form. The sampling rate of the ADC 28 is at lease twice the cut-off frequency of the low pass filter 27 to avoid the sampling alias. The digitized signal is sent to the microprocessor unit 30 for further analysis. The microprocessor unit contains an associated memory block 31. The data sampled from each row and each column of electrodes when the cage is empty is stored in the memory as calibration reference. When the animal is present the animal's body sitting on the electrode plate changes the electrodes' capacitance. The microprocessor unit 30 computes the differences between the data derived from the rows and the columns of the electrodes and the corresponding pre-stored reference data on the memory block 31. A larger difference indicates a larger variation in the capacitance change in the row or the column of the electrodes. The animal's location is determined by measuring the center of mass based on the data difference. To avoid interference from other objects under the electrode plate 10, the sine wave generated from the oscillator 29 is delivered to the shield layer 19 on the back side of the electrode plate 10 through an amplifier 25.

The relationship between the excitation signal from the oscillator amplifier 24 and the currently selected electrode, which is sending back the signal to the capacity detection circuit, may be configured in different ways. The preferred embodiment is shown in FIG. 7a. The excitation signal from the amplifier 24 is connected to the current selected electrode 15 and the receiving amplifier 23 through a resistor 32. The other non-active electrodes 16 (not being selected at the moment) are connected to ground. When an animal is present above the currently selected electrode 15, the capacity between the animal body 2 and the current selected electrode 15 shunts the excitation signal to other grounded electrodes 16. As a result, the amplitude of the received excitation signal drops at the input of the receiving amplifier 23, and the microprocessor senses a decreased data value in comparison with the reference data in which no animal is presented. The microprocessor can determine the animal's location based on the x-y coordinate of the electrodes which exhibit the decreased received excitation signal.

An alternative configuration of the excitation signal and the current selected electrode is shown in FIG. 7b. Currently selected electrode 15 is connected to the receiving amplifier 23 providing the input signal to the capacity detection circuit. The excitation signal from the amplifier 24 is connected to other non-active electrodes 16. When the animal is not present, only a small amount of excitation signal is coupled to the selected electrode through the capacity 7 in between the electrodes (see FIG. 5). When the animal is present above the selected electrode 15, the amplitude of the coupled excitation signal delivered to amplifier 23 increases due to the adding of capacity between the animal body and the electrodes. The microprocessor can determine the animal's location based on the x-y coordinates of the electrodes which exhibit the increment of the received excitation signal.

What is claimed is:

1. An apparatus for automatically tracking the location of animal comprised of:
    a. a walled enclosure;
    b. a plate made of electrical insulating material defining an animal floor thereat;
    c. a plurality of electrodes made of electrically conductive thin pieces, which are separated from each other by a predetermined space and wherein a plurality of capacities existing in between said electrodes, placed on the surface of said plate;
    d. a plurality of conductive wires connecting said electrodes in groups in such way that each electrode and its neighboring electrodes are not in the same group;
    e. means to measure the capacitances between said groups of electrodes and the neighboring electrodes;
    f. means to selectively establish electrical connection to any set groups of electrodes to said capacitances measuring means; and
    g. means to determine the location of the animal based on the changes of said capacitances.

2. Apparatus as defined in claim 1 wherein said electrodes placed on said plate cover the entire floor across said enclosure.

3. Apparatus as defined in claim 1 wherein said wires connecting said electrode groups are sequentially connected to said capacitance measure means by said capacitances measuring means by said selectively establishing electrical connection means.

4. Apparatus as defined in claim 1 wherein said capacitance measuring means comprises an electric signal generator, a signal conditioning circuit and an analog to digital converter.

5. Apparatus as defined in claim 4 wherein said electric signal generator provides an excitation signal to said selectively connected electrodes.

6. Apparatus as defined in claim 5 wherein said signal conditioning circuit receives and manipulates the excitation signal from said selectively connected electrodes by said selectively establishing electrical connection means.

7. Apparatus as defined in claim 6 wherein said analog to digital converter converts said excitation signal into a digitized value.

8. Apparatus as defined in claim 7 wherein said location determining means of the animal contains a calibration reference storage and a comparison unit.

9. Apparatus as defined in claim 8 wherein said calibration reference storage stores said digitized excitation signal when the animal is absent from said enclosure.

10. Apparatus as defined in claim 9 wherein said digitized excitation signal is continuously measured when the animal is present in the enclosure.

11. Apparatus as defined in claim 10 wherein said comparison unit determines the animal location by comparing said digitized excitation signal when the animal is present in the enclosure with said digitized excitation signal from the calibration reference storage.

\* \* \* \* \*